(12) United States Patent
Heide et al.

(10) Patent No.: US 10,307,526 B2
(45) Date of Patent: Jun. 4, 2019

(54) DEVICE AND METHOD FOR REGULATING A TREATMENT DEVICE

(71) Applicant: Fresenius Medical Care Deutschland GmbH, Bad Homburg (DE)

(72) Inventors: Alexander Heide, Eppstein (DE); Dejan Nikolic, Frankfurt (DE); Arne Peters, Bad Homburg (DE); Christoph Wiktor, Gelnhausen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 340 days.

(21) Appl. No.: 14/167,303

(22) Filed: Jan. 29, 2014

(65) Prior Publication Data
US 2014/0209537 A1 Jul. 31, 2014

Related U.S. Application Data

(60) Provisional application No. 61/758,485, filed on Jan. 30, 2013.

(30) Foreign Application Priority Data

Jan. 30, 2013 (DE) .................. 10 2013 001 587

(51) Int. Cl.
*A61M 1/36* (2006.01)
*A61M 1/16* (2006.01)
*A61M 1/34* (2006.01)

(52) U.S. Cl.
CPC ............ *A61M 1/3663* (2013.01); *A61M 1/16* (2013.01); *A61M 1/1605* (2014.02);
(Continued)

(58) Field of Classification Search
CPC ........ A61M 1/16; A61M 1/1647; A61M 1/34; A61M 1/341; A61M 1/3427; A61M 1/3663
(Continued)

(56) References Cited

U.S. PATENT DOCUMENTS

| 4,381,999 A * | 5/1983 | Boucher ............. B01D 61/145 210/637 |
| 5,792,367 A | 8/1998 | Mattisson et al. |

(Continued)

FOREIGN PATENT DOCUMENTS

| DE | 69528156 | 2/2003 |
| DE | 69530357 | 10/2003 |

(Continued)

*Primary Examiner* — Dirk R Bass
(74) *Attorney, Agent, or Firm* — Jacobson Holman, PLLC.

(57) ABSTRACT

A method and a device are disclosed for regulating an ultrafiltration in a dialysis treatment, in which the blood to be ultrafiltered in an extracorporeal blood circulation (109) flows through a blood chamber (110) of a dialyzer (113), which is subdivided by a semipermeable membrane (111) into a blood chamber (110) and a dialysis fluid chamber (108), and dialysis fluid in a dialysis fluid circulation (109) flows through the dialysis fluid chamber (108) of the dialyzer (113). The device has a blood pump (115) for controlling a blood flow in the extracorporeal blood circulation (112), a dialysis fluid pump (107) for controlling a dialysis fluid flow in the dialysis fluid circulation (109) upstream or downstream from the dialyzer (113), for controlling the dialysis fluid flow upstream of downstream from the dialyzer, a balancing device (104) for setting up a fluid balance in the dialysis fluid circulation between an inflow (106) and an outflow (105) of the dialysis fluid chamber (113) as a measure of the ultrafiltration, as well as a regulating unit (101) for regulating the blood pump (115), the throttle (117)

(Continued)

and/or the dialysis fluid pump (107). The pumps or the throttles (117) are regulated so that a predetermined ultrafiltration is achieved.

23 Claims, 5 Drawing Sheets

(52) U.S. Cl.
CPC ........ *A61M 1/1613* (2014.02); *A61M 1/1647* (2014.02); *A61M 1/34* (2013.01); *A61M 1/341* (2014.02); *A61M 1/3427* (2014.02); *A61M 1/3607* (2014.02); *A61M 2205/3334* (2013.01); *A61M 2205/3365* (2013.01)

(58) Field of Classification Search
USPC .................................................. 210/137, 647
See application file for complete search history.

(56) References Cited

U.S. PATENT DOCUMENTS

| | | | |
|---|---|---|---|
| 5,861,555 A | 1/1999 | Hobro et al. | |
| 6,280,632 B1 | 8/2001 | Polaschegg | |
| 2005/0131332 A1* | 6/2005 | Kelly | A61M 1/1696 604/4.01 |
| 2013/0075314 A1* | 3/2013 | Nikolic | A61M 1/14 210/143 |
| 2013/0292312 A1* | 11/2013 | Heide | A61M 1/3663 210/137 |

FOREIGN PATENT DOCUMENTS

| | | |
|---|---|---|
| EP | 0904789 | 3/1999 |
| WO | WO 95/22743 | 8/1995 |
| WO | WO 99/67615 | 12/1999 |
| WO | WO 01/89599 | 11/2001 |
| WO | WO 2005/044339 | 5/2005 |

* cited by examiner

DEVICE AND METHOD FOR REGULATING A TREATMENT DEVICE

TECHNICAL FIELD

The present invention relates to a method and a device for regulating a treatment device, in particular for regulating ultrafiltration in a dialysis treatment.

BACKGROUND

Dialysis is a process for purifying the blood of patients with acute or chronic renal insufficiency. A fundamental distinction is made here between methods having an extracorporeal blood circulation, such as hemodialysis, hemofiltration or hemodiafiltration, and peritoneal dialysis, which does not use an extracorporeal blood circulation.

In hemodialysis, blood in an extracorporeal circulation is passed through the blood chamber of a dialyzer, which is separated from a dialysis fluid chamber by a semipermeable membrane. A dialysis fluid containing the blood electrolytes in a certain concentration flows through the dialysis fluid chamber. The substance concentration of blood electrolytes in the dialysis fluid corresponds to the concentration in the blood of a healthy person. During the treatment, the patient's blood and the dialysis fluid are passed by both sides of the semipermeable membrane, usually in countercurrent at a predetermined flow rate. The substances that are eliminated in urine diffuse through the membrane from the blood chamber into the chamber for dialysis fluid, whereas electrolytes which are present in the blood and in the dialysis fluid at the same time diffuse from the chamber of higher concentration to the chamber of the lower concentration. If a pressure gradient from the blood side to the dialysis side is established on the dialysis membrane, water will diffuse out of the patient's blood, through the dialysis membrane and into the dialysis circulation, i.e., the so-called ultrafiltrate. This process of ultrafiltration leads to the desired withdrawal of water from the patient's blood.

In hemofiltration, ultrafiltrate is withdrawn from the patient's blood by applying a transmembrane pressure in the dialyzer or hemofilter, without any dialysis fluid being passed by the side of the membrane of the dialyzer on the patient's blood side. In addition, a sterile and pyrogen-free substitute solution may also be added to the patient's blood. We speak of predilution or post-dilution, depending on whether this substitute solution is added upstream or downstream from the dialyzer or hemofilter. The mass exchange takes place by convection in hemofiltration.

A combination of hemodialysis and hemofiltration occurs when substitute is added to the patient's blood simultaneously during a dialysis treatment. This form of treatment, which is also known as hemodiafiltration, is also covered by the concepts of hemodialysis, dialysis or dialysis treatment in the following discussion.

It is of crucial importance in a dialysis treatment that the removal of fluid is measured and balanced with great accuracy because there could be serious consequences for the patient even if the withdrawal of fluid is only slightly too great.

This is ensured by the fact that the inflow of dialysate or dialysis fluid into the dialysis fluid chamber and the outflow of dialysis fluid out of the dialysis fluid chamber are controlled separately from one another. The balance between the quantity of fluid added to the dialysis fluid chamber and the quantity of fluid withdrawn from the dialysis fluid chamber at the same time provides a measure of the ultrafiltrate withdrawn from the patient blood.

One possibility for balancing is to use balance chamber pumps based on the principle that a quantity of fluid supplied in an inflow to the dialysis fluid chamber corresponds to a quantity of fluid withdrawn in an outflow out of the dialysis fluid chamber.

For the additional withdrawal of fluid from the patient, another flow path with a delivery device, a so-called ultrafiltration pump, is set up in parallel with the blood chamber. The fluid to be withdrawn is passed through the parallel flow path going past the balance chamber and is measured by the ultrafiltration pump and thus forms a measure of the fluid balance.

Balance chambers have a complex structure and make high demands of the manufacturing tolerance.

As an alternative, the ultrafiltration could be controlled by controlling the flow rate in the inlet line to the dialysis fluid chamber and the flow rate in the outlet line out of the dialysis fluid chamber by pumps which can be controlled independently of one another and are arranged in the inlet line and in the outlet line. In this case, the balancing is performed by flow sensors arranged in the inlet line and the outlet line or by carts, which is associated with a great complexity for the calibration of these sensors or carts.

Therefore the object of the present invention is to overcome at least one of the aforementioned problems and to make available a simple device and a corresponding method for regulating ultrafiltration.

SUMMARY

This object is achieved by a device for regulating an ultrafiltration in a dialysis treatment of the blood to be ultrafiltered in an extracorporeal blood circulation; this blood flows through a blood chamber of a dialyzer which is subdivided by a semipermeable membrane into a blood chamber and a dialysis fluid chamber, and dialysis fluid flows through the dialysis fluid chamber of the dialyzer in a dialysis fluid circulation. The device according to the disclosure has a blood pump for controlling the blood flow in the extracorporeal blood circulation, a dialysis fluid pump arranged in the dialysis fluid circulation in an inflow to the dialyzer for controlling a dialysis fluid flow in the inflow, a throttle arranged in the dialysis fluid circulation in an outflow out of the dialyzer for controlling the dialysis fluid flow in the outflow, a balancing device for creating a liquid balance in the dialysis fluid circulation between the inflow to the dialysis fluid chamber and the outflow out of the dialysis fluid chamber as a measure of the ultrafiltration as well as a regulating unit for regulating the blood pump, the dialysis fluid pump and/or the throttle, so that a predetermined ultrafiltration is achieved.

In an alternative embodiment, the throttle is arranged upstream from the dialyzer in the inflow to the dialysis fluid chamber, and the dialysis fluid pump is arranged downstream from the dialyzer in the outflow out of the dialysis fluid chamber.

In addition, the present object is achieved by a device according to Claims 1 and 2 and a method according to Claim 12 or 13 for regulating an ultrafiltration in a dialysis treatment. Furthermore, the present object is achieved by a device according to Claim 8 and the method according to Claim 17 for regulating hemofiltration in a hemofiltration treatment. Advantageous embodiments are given in the dependent claims.

The arrangement of the dialysis fluid pump in the dialysis fluid circulation in an inflow to the dialysis fluid chamber means that the dialysis fluid pump is arranged close to a dialysis fluid preparation.

The inventors have recognized that with this configuration for regulating the dialysis fluid flow, no additional dialysis fluid pump downstream from the dialysis fluid chamber is necessary. This is associated with a reduced structural complexity. The situation is similar when the dialysis fluid pump is arranged in the outflow out of the dialysis fluid chamber. In this configuration, no additional dialysis fluid pump is necessary for regulating the dialysis fluid flow upstream from the dialysis fluid chamber.

The blood pump is advantageously arranged in the blood circulation in an inlet line to the blood chamber. In this way, the pressure supplied by the blood pump contributes to an excess pressure in the blood chamber in comparison with the dialysis fluid chamber.

The ultrafiltration may be regulated so that a predetermined value can be set for the blood flow rate or for the pressure applied by the blood pump and the regulating unit regulates the ultrafiltration in that the dialysis fluid pump and/or the throttle is regulated and controlled as a function of a measured ultrafiltration rate in that a pressure or a volume flow in an inlet line to the dialysis fluid chamber is regulated in the dialysis fluid circulation and the throttle resistance is regulated accordingly.

As an alternative, the ultrafiltration may also be regulated, so that predetermined values can be set for the dialysis fluid rate or a delivery pressure of the dialysis fluid pump and for the throttle value, and the regulating unit regulates the ultrafiltration in that it regulates the blood pump as a function of a measured ultrafiltration rate by regulating the pressure or the volume flow in an inlet line to the blood chamber in the extracorporeal blood circulation.

However, any other regulation of the ultrafiltration is also possible as long as the pressure conditions in the dialyzer can be controlled and/or regulated through the blood pump in the blood circulation and through the dialysis fluid pump and the throttle in the dialysis fluid circulation, so that the desired ultrafiltration takes place.

The throttle may be designed as a throttle with a variably adjustable cross section as the flow rate, as a clocked valve or as another component whose fluid resistance is variably adjustable, including a variably adjustable fluid resistance which is obtained only by averaging over time.

In a refinement of the device, the balancing device has a differential flow-measuring unit for measuring the differential flow between a flow in the inflow to the dialysis fluid chamber and the flow out of the dialysis fluid chamber, a branch of the inflow or the outflow to the branch of the dialysis fluid from the inflow or the outflow into another flow path as well as a device for adjusting the flow rate in the inflow, in the outflow and/or in the additional flow path which can be controlled so that the measured differential flow fulfills a predetermined condition. In this refinement, the device also has an apparatus for determining the flow rate in the additional flow path as a measure of the fluid balance.

The flow in the additional flow path may be adjusted approximately with a pump or a throttle arranged in the flow path.

DETAILED DESCRIPTION OF THE FIGURES

Figure 1:
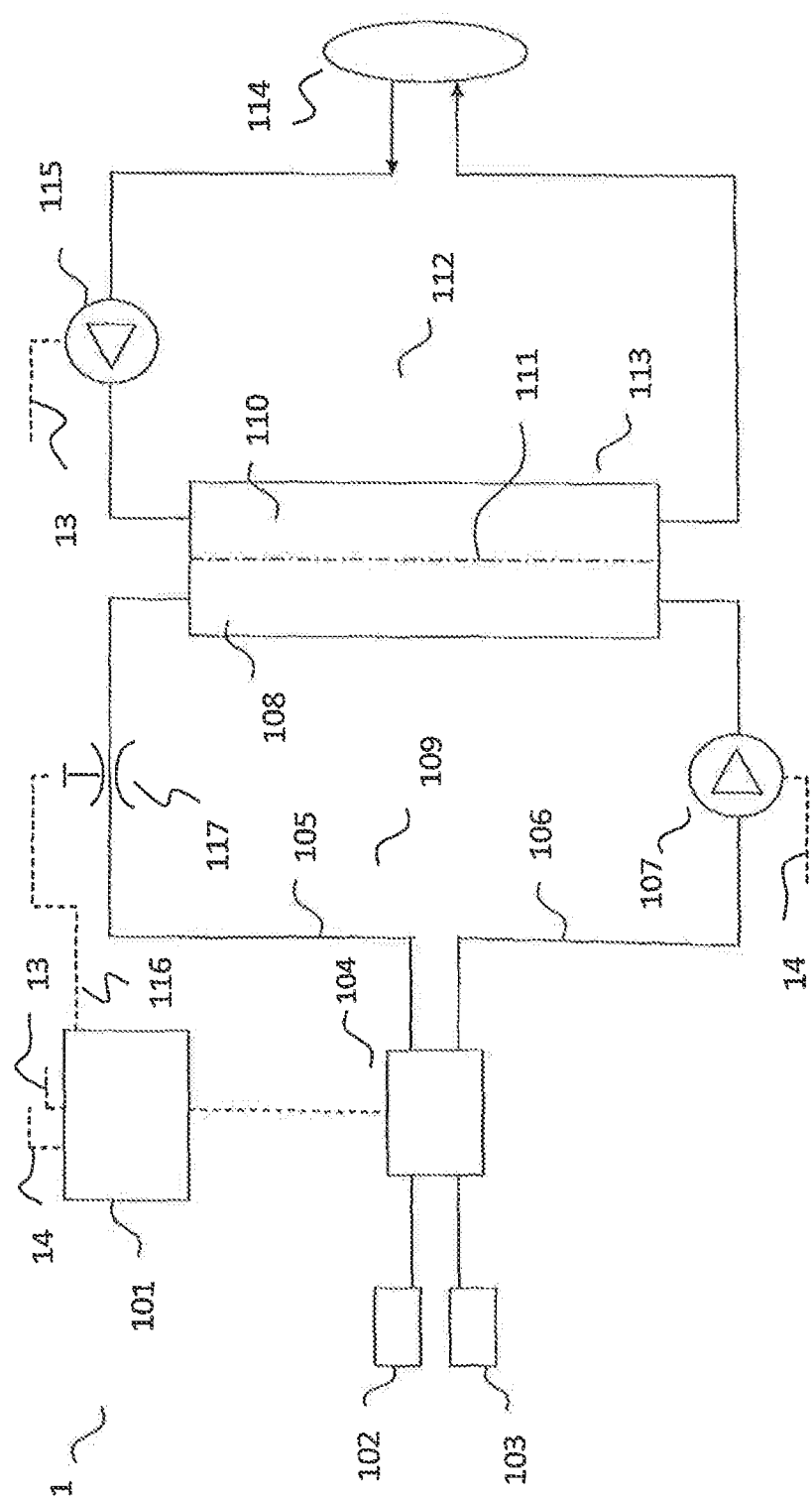
FIG. 1 shows a block diagram of a dialysis machine with a device for regulating the ultrafiltration.

FIG. 1 shows schematically a dialysis machine 1 with an apparatus for regulating the ultrafiltration in accordance with the teaching of the present invention. The blood to be treated is taken from the patient through an access 114 and is returned to the patient through the access 114 and through a blood chamber in the dialyzer 113 by means of a pump 115 in the extracorporeal blood circulation 112. The access 114 connects the blood circulation 112 to a blood vessel of the patient, which is suitable for taking blood and returning it. The access 114 may contain a separate inflow and outflow (double needle method) for taking blood and returning blood or the inflow and outflow may be designed as one element (single needle method).

In the dialyzer 113 a semipermeable membrane 111 separates a dialysis fluid chamber 108 from a blood chamber 110. A fluid exchange and a mass exchange take place through the semipermeable membrane 111, from the blood chamber 110 into the dialysis fluid chamber 108. Dialysis fluid in the dialysis fluid circulation 109 is transported through the dialysis fluid chamber 108 of the filter 113 by a dialysis fluid pump 107 in an inlet line 106 upstream from the dialysis fluid chamber. Furthermore, the dialysis fluid flow in the outlet line 105 from the dialysis fluid chamber 108 is controlled by means of the variably adjustable throttle 117. Alternatively the dialysis fluid pump 107 may also be arranged in the outlet line 105 downstream from the dialysis fluid chamber 108, and the control of the dialysis fluid flow in the inlet line 106 is accomplished by a variably adjustable throttle 107. A balancing device 104 is arranged in the dialysis fluid circulation 109 which is supplied from a dialysis fluid source 103 for balancing the dialysis fluid that is supplied to the dialysis fluid chamber 108 and flows out of the dialyzer 113. To this end, the flow rate in the inflow to the dialysis fluid chamber 108 and the flow rate in the outflow from the dialysis fluid chamber 108 may be detected separately or a differential flow may be determined as a measure of the fluid balance. The fluid balance corresponds to the ultrafiltration quantity withdrawn through the membrane 111 in the dialyzer 113. So-called spent dialysis fluid flowing out of the dialyzer 113 is usually discarded in a dialysis fluid outflow 102. Alternatively, regeneration of spent dialysis fluid may be provided.

In addition, in the case of hemodiafiltration upstream or downstream from the dialyzer 113 in the blood circulation 512, substitution fluid may be added through a substituate line (not shown). In this case, the added quantity of substituate is also to be taken into account in the total fluid balance.

The pressure conditions prevailing on the membrane 111 in the dialyzer 113 are influenced through the control of the blood pump 115, the control of the dialysis fluid pump 107 and/or the control of the variably adjustable throttle 117 in such a way that an excess pressure prevails in the blood chamber 110 in comparison with the dialysis fluid chamber 108. Therefore fluid is transported through the membrane from the blood chamber 110 into the dialysis fluid chamber 108.

The blood pump 115 may be controllable to achieve a certain pump rotational speed or a certain blood flow rate as an operating parameter for example in an embodiment as a peristaltic pump. Alternatively the blood pump 115 may be controllable for achieving a certain delivery pressure as an operating parameter, e.g., as an impeller pump.

Likewise the dialysis fluid pump 107 may be designed as a peristaltic pump, a diaphragm pump, a piston pump or the like to achieve a certain delivery rate or pump rotational speed, or it may be designed as an impeller pump, for example, to build up a certain delivery pressure.

The variably adjustable throttle 117 may be designed as a throttle having a variably adjustable cross section as a through-flow, as a clocked valve or as some other component whose fluid resistance is variably adjustable, including a variably adjustable fluid resistance which is obtained only by averaging over time.

A control and regulating unit 101 which is connected to the balancing device 104 via a measuring line is connected via the control line 13 to the blood pump 115, via the control line 14 to the dialysis fluid pump 107 and via the control line 116 to the variably adjustable throttle 117. During the blood treatment, current measured parameters of ultrafiltration such as the ultrafiltration quantity or ultrafiltration rate are transmitted from the balancing device to the control and regulating unit 101 either continuously or periodically. The control and regulating unit 101 uses the current measured parameters to derive control signals for the blood pump 115, the dialysis fluid pump 107 and for the variably adjustable throttle 117. The control of the dialysis fluid pump 107, the blood pump 115 and the variably adjustable throttle 117 then takes place with regard to an ultrafiltration that is to be achieved, such as a certain ultrafiltration rate or a certain ultrafiltration volume to be achieved over the course of treatment.

The regulation may take place in such a way that the blood pump 115 and the dialysis fluid pump 107 are operated at a constant rotational speed or at a constant delivery pressure, and the variably adjustable throttle 117 is controlled so that the ultrafiltration value transmitted by the balancing device 104 serves as a regulated variable. If for example the transmitted measured value of the ultrafiltration rate is above a corresponding setpoint value, then the variably adjustable throttle 117 is to be constricted or, in other words, its flow resistance is to be increased. If the ultrafiltration rate is below its setpoint value, then the variably adjustable throttle 117 is widened or in other words its flow resistance is reduced.

An alternative control strategy is such that the blood pump 115 is operated at a constant rotational speed or at a constant delivery pressure, the variably adjustable throttle 117 is set at a certain flow resistance and the dialysis fluid pump 107 is controlled so that the ultrafiltration value transmitted by the balancing device 104 serves are the control variable. If, for example, the transmitted value of the ultrafiltration rate is above a corresponding setpoint value, then the dialysis fluid pump 107 is to be accelerated, but if the ultrafiltration rate is below its setpoint value, then the dialysis fluid pump 107 is throttled.

Another alternative control strategy may be to operate the dialysis fluid pump 107 at a constant rotational speed or at a constant delivery pressure, to set the variably adjustable throttle 117 at a certain flow resistance and to control the blood pump 115 so that the ultrafiltration value transmitted by the balancing device 104 is regulated. If for example the transmitted value of the ultrafiltration rate is above a corresponding setpoint value then the blood pump 115 is to be throttled, but if the ultrafiltration rate is below its setpoint value, the blood pump 115 is to be accelerated.

A combination of control strategies is possible, for example in such a manner that in an internal control loop, first the blood pump 115 and/or the dialysis fluid pump 107 is operated at a constant level and the variably adjustable throttle 117 is controlled. Only when the throttle is completely opened are the blood pump 115 and/or the dialysis fluid pump 107 controlled accordingly.

The ultrafiltration may be regulated so that a certain value is preselected for the ultrafiltration rate. Alternatively, a certain ultrafiltration profile may be predetermined for the ultrafiltration volume to be withdrawn during the blood treatment.

The predetermined value of the ultrafiltration rate may be a constant or continuously changing value for the ultrafiltration rate.

Alternatively, a profile may be preselected for the ultrafiltration rate or the ultrafiltration volume such that intervals with a positive ultrafiltration rate and Intervals with a negative ultrafiltration rate are in alternation in this profile. In this way a so-called push-pull mode can be achieved in which deposits are released from the dialyzer membrane or the deposition of substances on the dialyzer membrane is reduced or prevented. This improves the permeability of the dialyzer membrane and improves the corresponding cleaning performance (clearance) for agent molecules. The present arrangement achieves this with a small equipment complexity, for example without an additional pump for applying oscillating pressure pulses. Thus a push-pull mode can be achieved exclusively through suitably clocked control of the variably adjustable throttle 117.

The regulation of ultrafiltration may in this case take place by analogy with the regulating strategies described above for the ultrafiltration rate so that instead of a comparison with the setpoint value for the ultrafiltration rate, there is a corresponding comparison with an ultrafiltration profile.

In the case of hemodiafiltration, the quantity of substituate added to the fluid balance through the substituate line during the treatment can be adjusted and the resulting total ultrafiltration rate, i.e., the difference between the quantity of fluid withdrawn via the dialyzer and the substituate weight, is used as a regulated variable.

Figure 2:
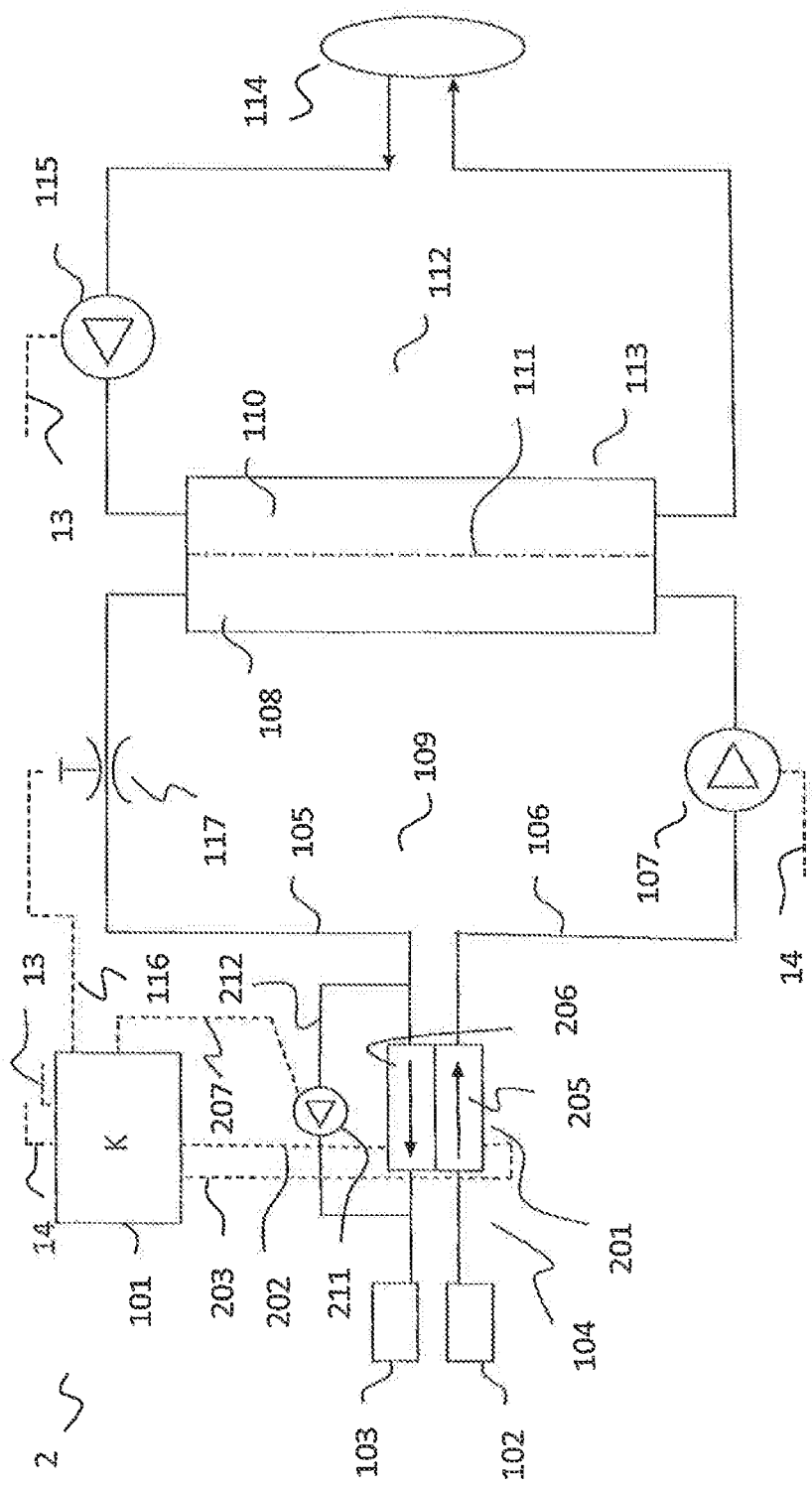
FIG. 2 shows a block diagram of another dialysis machine having another apparatus for regulating the ultrafiltration.

FIG. 2 shows schematically another dialysis machine with another device for regulating ultrafiltration. The dialysis machine shown in FIG. 2 corresponds essentially to the design of the ultrafiltration device in FIG. 1. Reference is made to the description of the corresponding elements instead of repeating that description here. The depiction of the ultrafiltration device differs fundamentally through the embodiment of the balancing device 104, which is described in greater detail below.

The balancing device 104 comprises the flow-measuring cells 205 and 206 which are connected to a differential flow sensor 201, so that the flow-measuring cell 205 is situated upstream from the dialysis fluid chamber 108 and the flow-measuring cell 206 is situated downstream from the dialysis fluid chamber 108 in the dialysis fluid circulation 109.

An ultrafiltration pump 211 is situated in a fluid path 212, which is parallel to the flow-measurement cell 206 and in which the fluid transport is controlled by the ultrafiltration pump 211.

Instead of the ultrafiltration pump 211, a throttle may also be provided to control the flow in the parallel fluid path 212.

The differential flow sensor 201 determines a pair of measured values consisting of a separate measured value for each flow-measuring cell 205 and 206, which indicates the flow rate of the fluid through the respective flow-measuring cell. The pair of measured values is preferably determined one or more times per second and transmitted over measurement lines 202 and 203 to the control and regulating unit 101. The control and regulating unit 101 assigns a pair of volume flow values to each measured value pair such that a plot of a measured value on a volume flow may be used, this plot being based on a calibration performed previously. Alternatively, a plot on a mass flow could also be used. The control and regulating unit 101 derives a control signal for the pump 211 from the volume flow pair thereby determined approximately, so that the pump 211 is operated in such a way that the volume flow through the two flow-measuring cells 205 and 206 of the differential flow sensor corresponds at each point in time. For example, the control and regulating unit 101 forms a differential signal from the two volume flows of the volume flow pair and alters the flow rate of the ultrafiltration pump 211 by increasing it or decreasing it, depending on the differential signal, in a suitable manner, so that the differential signal becomes negligible toward zero. If the flow through the flow-measuring cell 205 is less than the flow through the flow-measuring cell 206, this yields a positive value for the difference in the measured values of the flow-measuring cell 206 and the flow-measuring cell 205. The control and regulating unit 101 can then alter the control signal for the ultrafiltration pump 211 so that the flow rate through the ultrafiltration pump 211 is increased, and the flow rate through the flow-measuring cell 206 is reduced, while there is no change in flow in the outflow from the dialyzer, until the same flow is established as that through the flow-measuring cell 205. The flow rate through the ultrafiltration pump 211 then indicates the differential flow between the dialysis fluid flow coming out of the dialysis fluid chamber and the dialysis fluid flow entering the dialysis fluid chamber. The flow rate through the ultrafiltration pump 211 is then a measure of the quantity of ultrafiltrate withdrawn from the dialyzer 113.

In one embodiment, the flow rate through the ultrafiltration pump 211 is set at a predetermined value and the control of the blood pump 115, of the dialysis fluid pump 107 and of the variably adjustable throttle 117 takes place as described above, so that the differential flow measured in the differential flow sensor 201 fulfills a predetermined condition such as "becoming negligible toward zero."

The flow rate through the ultrafiltration pump 211 is a measure of the fluid balance between the inflow to the dialyzer 113 and the outflow out of the dialyzer 113, i.e., for the quantity of ultrafiltrate withdrawn from the dialyzer 113.

The disappearance of the differential signal may relate to a differential flow at a certain point in time or to the disappearance of an integral of a differential flow.

In another embodiment the assignment of the measured value pair to a volume flow or mass flow may be omitted if the difference in the measured values at the same volume flow through both channels is known. In this case, the control and regulating unit 101 forms the difference between the two measured values and alters approximately the permeability of the variably adjustable throttle 117 in a suitable manner until the difference corresponds to the previously known difference at the same volume flow.

The differential flow sensor 201 may advantageously function according to the magnetic inductive principle in which each of the two flow-measuring cells 205, 206 through which the flow passes in countercurrent has a rectangular cross section and is arranged at a right angle to a magnetic field. The magnetic field is adjusted by the control of the differential flow sensor 201 and is of such properties that a homogeneous field of the same size prevails through both flow-measuring cells 205 and 206. This is achieved, for example, by the fact that the channels of the flow-measuring cells 205, 206 are arranged one above the other with respect to the magnetic field. In each channel, an electrode is mounted on the inner wall extending along the magnetic field, so that the electrode is opposite and at a right angle to the magnetic field and to the direction of flow in the respective channel. If fluid flows through the channel, then a charge separation of the ions present in the liquid is accomplished by the magnetic field, so that an electric voltage is applied to the electrodes. This voltage is proportional to the velocity of flow and depends on the magnetic field strength. If the magnetic fields in the two flow-measuring cells 205 and 206 are each of the same size, then the magnetic field strength dependence for the relative differential flow signal is advantageously eliminated in forming a differential signal from the two channels.

In other words, disappearance of the differential signal indicates that the flow through the flow-measuring cell 205 and the flow through the flow-measuring cell 206 are equal in size, regardless of the absolute size of the magnetic field in the flow-measuring cells 205 and 206.

In the embodiment in which a profile is preselected for the ultrafiltration rate or for the ultrafiltration volume, in which intervals with a positive ultrafiltration rate alternate with intervals with a negative ultrafiltration rate, the predetermined condition is advantageously met when the integral of the ultrafiltration rate and/or the integral of the differential signal becomes negligible toward zero.

The ultrafiltration pump 211 is preferably selected from the group of displacement pumps, more preferably a diaphragm pump, a tube roll pump, a piston pump or a gear pump or any other type of pump that makes it possible to determine the quantity of liquid pumped. For example, the volume delivered by a tube roll pump can be determined by the pump tube volume and the angle of rotation of the rotor of the tube roll pump with good accuracy using known methods. Corresponding methods for determining the quantity of liquid pumped are known from the state of the art for other pumps from the group of displacement pumps.

It is advantageous here that the quantity of liquid to be measured corresponds to the ultrafiltrate quantity. This quantity is typically 3-5 liters per dialysis treatment or day, whereas the quantity of dialysate flowing through the flow sensor is a multiple thereof, typically 60-240 liters. Therefore, in accordance with the present disclosure, it is advantageously possible to use measurement devices or measurement methods for the differential flow that must have a significantly lower tolerance than the measurement methods which detect the quantity of dialysate flowing in and flowing out separately and form a difference only thereafter.

Figure 3:
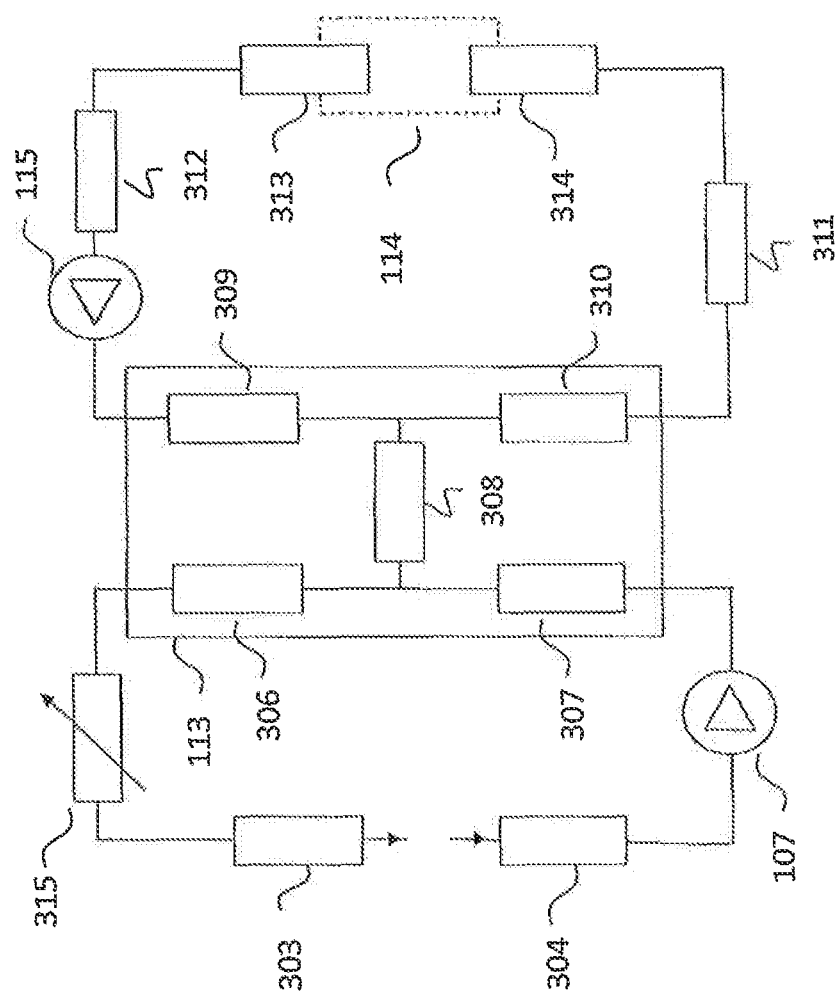
FIG. 3 shows a block diagram of a basic diagram for a dialysis machine.

FIG. 3 shows an equivalent circuit diagram for the dialysis machine illustrated in FIG. 1 with the dialysis fluid pump 107, the blood pump 115 and the dialyzer 113, such that the flow resistances in the dialysis fluid circuit, in the blood circulation and in the dialyzer are depicted as resistances of an electric equivalent diagram. In detail, an arterial needle resistance 313, an arterial line resistance 312, a venous needle resistance 314, a venous line resistance 311 are depicted in the extracorporeal blood circulation, and an arterial filter longitudinal resistance 309 and a venous filter longitudinal resistance 310 are depicted in the dialyzer 113. The flow resistances in the dialysis fluid circulation are modeled by a flow resistance of the dialyzer 307 on the input end, a flow resistance of the dialyzer 306 on the output end, a flow resistance 304 on the dialysate inlet side of the dialysis fluid circulation, a fixedly predetermined flow resistance 303 on the dialysate output side of the dialysis fluid circulation and by a variable throttle resistance 315, i.e., the variable resistance of the adjustable throttle 117. The membrane in the dialyzer is modeled by a transmembrane resistance 308. The designations of the individual resistances, their reference notation as well as the formulas used in the derivation are shown in Table 1 for the derivation for dimensioning the resistances in the dialysis fluid circulation, in the extracorporeal blood circulation and the transmembrane resistance as given below.

TABLE 1

| Identification of the Resistance | Reference numeral | Equation symbol |
| --- | --- | --- |
| arterial needle resistance in the extracorporeal blood circulation | 313 | $R_{aN}$ |
| arterial line resistance in the extracorporeal blood circulation | 312 | $R_{aL}$ |
| venous needle resistance in the extracorporeal blood circulation | 314 | $R_{vN}$ |
| venous line resistance in the extracorporeal blood circulation | 311 | $R_{aN}$ |
| arterial filter longitudinal resistance | 309 | $R_{aF}$ |
| venous filter longitudinal resistance | 310 | $R_{vF}$ |
| flow resistance at the input end in the dialysis fluid circulation | 304 | $R_{Din}$ |
| flow resistance at the output end in the dialysis fluid circulation | 303 | $R_{Dout}$ |
| flow resistance at the input end of the dialyzer | 307 | $R_{DFin}$ |
| flow resistance at the output end of the dialyzer | 306 | $R_{DFout}$ |
| transmembrane resistance | 308 | $R_{TM}$ |
| throttle resistance | 315 | $R_{Dr}$ |

Figure 4:
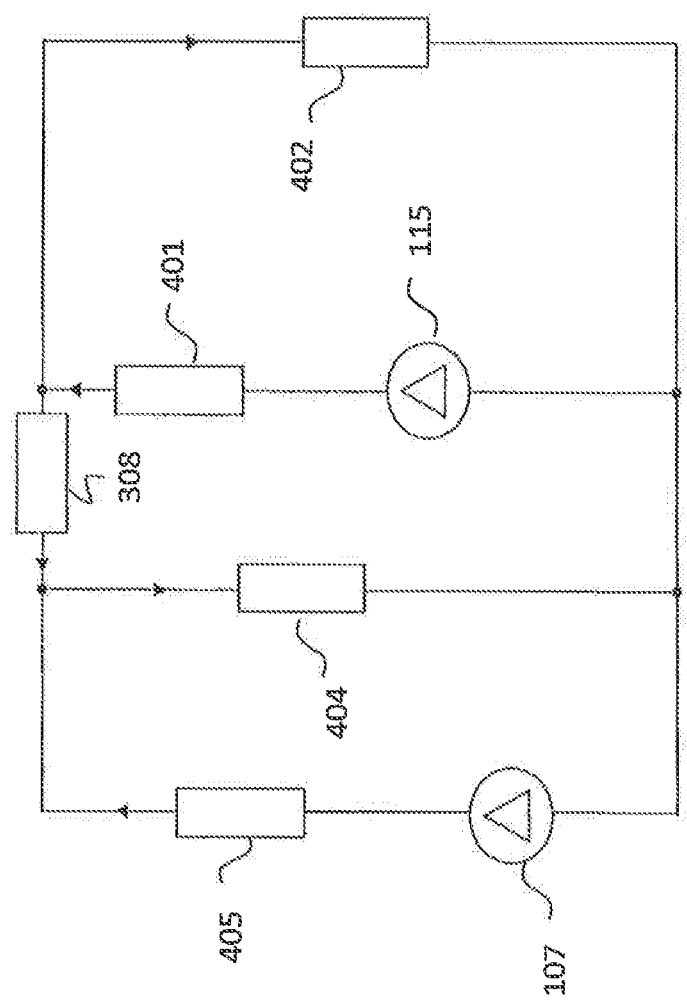
FIG. 4 shows a block diagram of a simplified electric circuit diagram for a dialysis machine.

FIG. 4 shows a simplified equivalent circuit diagram of the electric circuit diagram shown in FIG. 3. In the simplified circuit diagram shown in FIG. 4 the arterial needle resistance in the extracorporeal blood circulation (symbol: $R_{aN}$) and the arterial line resistance in the extracorporeal blood circulation (symbol: $R_{aL}$) as well as the arterial filter longitudinal resistance (symbol: $R_{aF}$) are combined into a total arterial resistance 401 (symbol: $R_a$) as follows:

$$R_a = R_{aN} + R_{aL} + R_{aF} \quad \text{(equation 1)}$$

Likewise, the venous needle resistance in the extracorporeal circulation (symbol: $R_{vN}$), the venous line resistance (symbol: $R_{vL}$) in the extracorporeal blood circulation as well as the venous filter longitudinal resistance (symbol: $R_{vF}$) are combined to yield a total venous resistance 402 (symbol: $R_v$) as follows:

$$R_v = R_{vN} + R_{vL} + R_{vF} \quad \text{(equation 2)}$$

A corresponding combination of resistances in the dialysis fluid circulation yields the following. The flow resistance at the input end in the dialysis fluid circulation 304 (symbol: $R_{Din}$) and the flow resistance 307 at the input end of the dialyzer (symbol: $R_{DFin}$) can be combined into an input resistance 405 (symbol: $R_{in}$) as follows:

$$R_{in} = R_{Din} + R_{DFin} \quad \text{(equation 3)}$$

The flow resistance at the output end in the dialysis fluid circulation 303 (symbol: $R_{Dout}$) and the flow resistance at the output end of the dialyzer 306 (symbol: $R_{DFout}$) can be combined to yield an output resistance 404 (symbol: $R_{out}$) as follows:

$$R_{out} = R_{Dout} + R_{DFout} + R_{Dr} \quad \text{(equation 4)}.$$

Table 2 below summarizes the names of the resistances shown in FIG. 4, their reference numerals and the symbols used in this derivation:

TABLE 2

| Name of the Resistance | Reference numeral | Symbol |
| --- | --- | --- |
| total arterial resistance | 401 | $R_a$ |
| total venous resistance | 402 | $R_v$ |
| input resistance (in the dialysis fluid circulation) | 405 | $R_{in}$ |
| output resistance (in the dialysis fluid circulation) | 404 | $R_{out}$ |
| transmembrane resistance | 308 | $R_{TM}$ |

The blood pump and the dialysis fluid pump can be modeled as a current source or as a voltage source, such that the suitable modeling is influenced by the design of the pump. Thus when using a displacement pump such as a diaphragm pump, a tube roll pump, a piston pump or a gear pump as the dialysis fluid pump, the modeling of the dialysis fluid pump as a current source is advantageous. The situation is similar when the blood pump is designed as a displacement pump, for example, as a tube roll pump. A constant-pressure pump such as an impeller pump is preferably modeled as a voltage source. If the blood pump or the dialysis fluid pump is modeled as a non-ideal voltage source or current source with corresponding internal resistances, then the respective internal resistances must add the resistances in the dialysis fluid circulation and/or in the extracorporeal blood circulation. Thus, in modeling the dialysis fluid pump as a non-ideal voltage source, for example, the flow resistance of the dialysis fluid pump must be included in the input resistance 405. The situation is similar for the extracorporeal blood circulation. Those skilled in the art are aware of the required considerations corresponding to this. Those skilled in the art will also be aware of how equivalent circuit diagrams in which non-ideal voltage sources are modeled are to be converted into corresponding equivalent circuit diagrams with non-ideal current sources.

The following considerations may be helpful in dimensioning the resistances in the extracorporeal blood circulation and in the dialysis fluid circulation as well as in the dimensioning of the internal resistances of the pumps involved and in controlling the pumps involved to achieve a desired ultrafiltration rate.

If a corresponding current $I_{UF}$ is assumed for the ultrafiltration rate in the electric equivalent diagram, then in the case of modeling of the pumps as voltage sources, the following equation for the ultrafiltration rate can be given in the case of modeling of the pumps as voltage sources if the dialysis fluid pump is modeled with a voltage source of the voltage $U_D$ and the blood pump is modeled with a voltage source of the voltage $U_B$:

$$I_{UF} = \frac{\dfrac{U_B \cdot R_V}{R_a + R_V} - \dfrac{U_D \cdot R_{out}}{R_{in} + R_{in}}}{\dfrac{R_a \cdot R_v}{R_a + R_v} + \dfrac{R_{in} \cdot R_{out}}{R_{in} + R_{out}}} \quad \text{(equation 5)}$$

In the case of modeling of the pumps as current sources, the following formula can be given for the ultrafiltration rate if the dialysis fluid pump is modeled with a current source of the current $I_D$ and the blood pump is modeled with a current source of the current $I_B$:

$$I_{UF} = \frac{I_B \cdot R_V - I_D R_D}{R_V + R_{out} + R_{TM}} \quad \text{(equation 6)}$$

The following consideration is helpful for the dimensioning of the output resistance 404 (symbol $R_{out}$). The switch in equation 6 for the output resistance 404 (symbol $R_{out}$) required to achieve a certain ultrafiltration rate yields the following equation:

$$R_{out} = \frac{R_V \cdot (I_B - I_{UF}) - R_{TM} I_{UP}}{I_D - I_{UP}} \quad \text{(equation 7)}$$

Equation 7 shows that if the transmembrane resistance $R_{TM}$ is too high, it has an unfavorable effect on the dimensioning of the output resistance $R_{out}$ in the dialysis fluid circulation. The transmembrane resistance $R_{TM}$ should therefore be selected to be as small as possible, for example as a filter with a high specific throughput coefficient ("high cutoff filter") or as a filter with a sufficiently large effective filter area. One point to be considered is that the transmembrane resistance $R_{TM}$, like the venous filter longitudinal resistance $R_{vF}$, will increase in the course of the extracorporeal blood treatment. The increase in the venous filter longitudinal resistance $R_{vF}$ in the extracorporeal blood circulation is typically based on the increase in hematocrit in the course of the blood treatment, the so-called hemoconcentration as well as a possible development of stenoses in the extracorporeal blood circulation. There is often an increase in the transmembrane resistance $R_{TM}$ in course of a blood treatment due to deposits on the dialyzer membrane. These effects which occur regularly in the course of a blood treatment must be taken into account in dimensioning the resistances in the extracorporeal blood circulation and in the dialysis fluid circulation as well as in controlling the blood pump, the dialysis fluid pump and the variably adjustable throttle.

The following numerical example can give an indication of a possible dimensioning of the flows involved, i.e., a minimal value $I_{Bmin}$=60 mL/min and maximal value $I_{Bmax}$=300 mL/min are assumed for the blood flow $I_B$, and a maximal value $I_{UFmax}=I_B/10$, i.e., approx. 20 mL/min and a minimal value $I_{UFmin}$=0 mL/min are assumed for the ultrafiltration rate $I_{UF}$ and a minimal value $I_{Dmin}=I_B/3$ and maximal value $I_{Dmax}$=200 mL/min are assumed for the dialysis fluid rate $I_D$.

The blood flow rate $I_B$ is set as the flow through the blood pump 115; the dialysis fluid rate $I_D$ corresponds to the flow through the dialysis fluid pump 107, and the ultrafiltration rate $I_{UF}$ corresponds to the flow through the transmembrane resistance 308.

In general, the following equation holds for the dialysis fluid rate $I_D$:

$$I_D = \frac{I_B \cdot R_V - I_{UF} \cdot (R_V + R_{out} + R_{TM})}{R_{out}} \quad \text{(equation 8)}$$

Fundamentally, with a given flow rate $I_B$, it holds that a maximal ultrafiltration rate is achieved when the dialysis fluid rate $I_D$ is at a minimum.

After rearranging, equation 8 yields the following equation:

$$I_{Dmin} \leq \frac{R_V}{R_{out}} \cdot (I_B - I_{UF}) - \left(1 + \frac{R_{TM}}{R_{out}}\right) I_{UF}. \quad \text{(equation 9)}$$

If $I_B$=50 mL/min is used as an alternative numerical value for the minimal blood flow and $I_{UF}$=5 mL/min is used as an alternative for the ultrafiltration rate, this yields the following equation, which relates the variables of the resistances $R_V$, $R_{out}$ and $R_{TM}$ to one another:

$$20 \leq \frac{R_V}{R_{out}} \cdot (50 - 5) - \left(1 + \frac{R_{TM}}{R_{out}}\right) 5 \quad \text{(equation 10)}$$

or:

$$25 \leq 45 \cdot \frac{R_V}{R_{out}} - 5 \cdot \frac{R_{TM}}{R_{out}} \quad \text{(equation 11)}$$

Starting with a certain ratio between the transmembrane resistance $R_{TM}$ and the output resistance in the dialysis fluid circulation, the following equations are obtained for dimensioning the output resistance $R_{out}$ in the dialysis fluid circulation with respect to the total venous resistance $R_V$. Increasing values are given for the transmembrane resistance $R_{TM}$, reflecting the abovementioned effects of an increase over the course of treatment.

$$R_{TM} = R_{out}/2 \;\rightarrow\; R_{out} \leq \frac{90}{55} R_V$$

$$R_{TM} = R_{out} \;\rightarrow\; R_{out} \leq \frac{45}{30} R_V$$

$$R_{TM} = 2 \cdot R_{out} \;\rightarrow\; R_{out} \leq \frac{45}{35} R_V$$

$$R_{TM} = 4 \cdot R_{out} \;\rightarrow\; R_{out} \leq \frac{45}{45} R_V$$

This example of a calculation shows that the output resistance $R_{out}$ must be selected to be smaller when the transmembrane resistance $R_{TM}$ is greater. As already mentioned above for the interpretation of the flow resistances in the dialysis fluid circulation and in the extracorporeal circulation, it is a disadvantage if the transmembrane resistance $R_{TM}$ is too high. For example, if it is assumed that the transmembrane resistance $R_{TM}$ can have as its maximum value four times the output resistance $R_{out}$ in the dialysis fluid circulation, then the numerical example given above yields the simple requirement that $R_{out}$ must be smaller than $R_V$. For the interpretation of the output resistance $R_{out}$ in the dialysis fluid circulation and the venous total resistance $R_V$ it is sufficient to formulate the total venous resistance $R_V$ at the start of the blood treatment because equation 9 is fulfilled sooner with a total venous resistance that rises during the blood treatment period.

The output resistance $R_{out}$ in the exemplary embodiments of FIGS. 1 and 2 is controlled by a corresponding adjustment of the throttle 117.

For the values given below as an example of the rate of the dialysis fluid flow $I_D$, the blood flow $I_B$ and the ultrafiltration rate $I_{UF}$ it is assumed that the value of the output resistance $R_{out}$ at the start of the treatment corresponds to the total venous resistance $R_V$ and that the transmembrane resistance $R_{TM}$ at the start of the treatment corresponds to the output resistance $R_{out}$.

At a maximum blood flow $I_B$=200 mL/min the maximum ultrafiltration rate $I_{UF}$=20 mL/min is achieved at a dialysis flow rate as follows:

$$I_D=(200-20)\text{mL/min}-2\cdot 20 \text{ mL/min}=140 \text{ mL/min}$$

starting from equation 9.

The minimal ultrafiltration rate $I_{UF}$=0 mL corresponds to a dialysis fluid rate $$I_D=(200-0)\text{mL/min}-2\cdot 0 \text{ mL/min}=200 \text{ mL/min}.$$

Both values are within an allowed, acceptable or preferred range of the dialysis fluid rate $I_D$<200 mL/min.

For the following numerical example, it is assumed that in the remaining course of the blood treatment the transmembrane resistance $T_M$ rises to a value four times higher as a result of the effects described above. To achieve a maximum ultrafiltration rate $I_{UF}$=20 mL/min, throttling of the dialysis fluid rate to $$I_D=(200-20)\text{mL/min}-5\cdot 20 \text{ mL/min}=80 \text{ mL/min}$$

would be necessary.

A dialysis fluid rate of $$I_D=(200-0)\text{mL/min}-5\cdot 0 \text{ mL/min}=200 \text{ mL/min}$$

would still have to be established for the minimal ultrafiltration rate $I_{UF}$=0 mL.

If it is assumed that as a result of the effects mentioned above, the total venous resistance $R_V$ is doubled in the course of the blood treatment, this yields a required dialysis fluid rate of $$I_D=2\cdot(200-20)\text{mL/min}-5\cdot 20 \text{ mL/min}=260 \text{ mL/min}$$

for the maximum ultrafiltration rate of 20 mL/min to be achieved.

For a minimal ultrafiltration rate $I_{UF}$=0 mL the result is a dialysis fluid rate of $$I_D=2\cdot(200-0)\text{mL/min}-5\cdot 0 \text{ mL/min}=400 \text{ mL/min}.$$

To be able to regulate the ultrafiltration rate over the entire range of 0 to 20 mL/min in this case, there is the possibility of expanding the range of the dialysis fluid flow considered acceptable, admissible or preferred or to reduce the blood flow $I_B$. Thus, for example, at a maximum allowed dialysis fluid flow $I_D$=200 mL/min, a maximal ultrafiltration rate $I_{UF}$=20 mL/min could be achieved at a blood flow rate $I_B$=170 mL/min and a minimal ultrafiltration rate $I_{UF}$=0 mL/min would be achieved at a blood flow rate $I_B$=100 mL/min.

The following sample calculation should illustrate how advantageous it is to keep the transmembrane resistance $R_{TM}$ low. If it is confirmed through the dimensioning of the dialyzer and the dialysis fluid circulation that the transmembrane resistance $R_{TM}$ corresponds at its maximum to the output resistance $R_{out}$ in the dialysis fluid circulation and if the dialysis fluid circulation and the extracorporeal blood circulation are designed so that the output resistance $R_{out}$ in the dialysis fluid circulation is in a ratio $R_{out}$=3/2 $R_V$ to the total venous resistance, then a maximal ultrafiltration rate of 20 mL/min is obtained at a flow rate $I_B$=200 mL/min and at a dialysis fluid rate of $$I_D=4/3\cdot(200-20)\text{mL/min}-2\cdot 20 \text{ mL/min}=200 \text{ mL/min}$$

and a minimal ultrafiltration rate of 0 mL/min is obtained at the same blood flow rate $I_B$ and at a dialysis fluid rate of $$I_D=4/3\cdot(200-0)\text{mL/min}-2\cdot 0 \text{ mL/min}=267 \text{ mL/min}.$$

The range of an ultrafiltration rate $I_{UF}$ of 0 mL/min to 20 mL/min can thus be controlled with a smaller variation in the dialysis fluid rate $I_D$.

Figure 5:
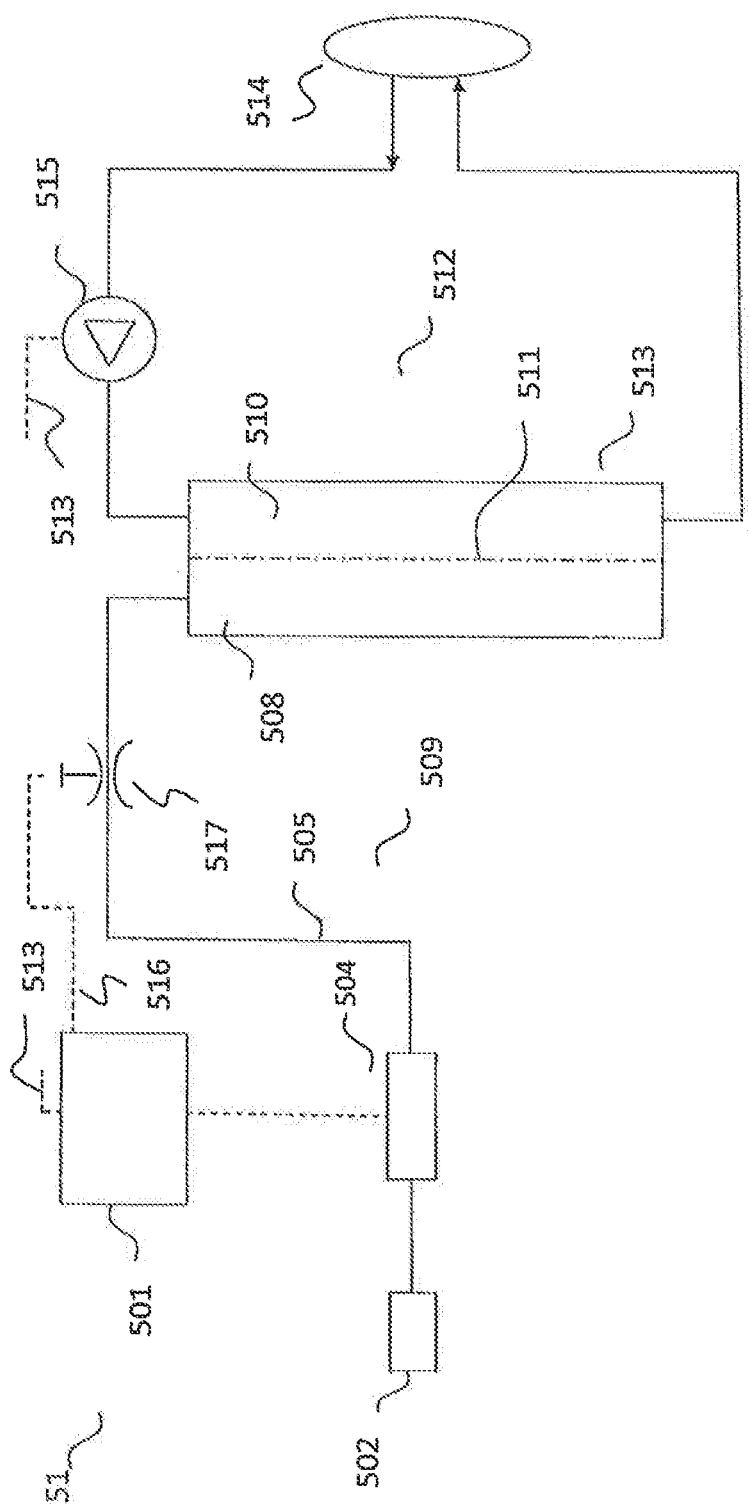
FIG. 5 shows a block diagram of a hemofiltration machine with an apparatus for regulating the hemofiltration.

FIG. 5 shows schematically a hemofiltration device 51 with a device for regulating the hemofiltration in accordance with the teaching of the present invention. The blood to be treated is taken from the patient via an access 514 and is returned to the patient through a blood chamber of the dialyzer or hemofilter 513 and through the access 514 by means of a blood pump 515 in the extracorporeal blood circulation 512. The access 514 connects the blood circulation 512 to a blood vessel of the patient which is suitable for taking blood and returning it. The access 114 may contain a separate outlet and inlet ("double needle" method) for taking blood and for returning blood or the inflow and outflow may be designed as one element ("single needle" method). Upstream or downstream from the dialyzer or hemofilter 513, substitution fluid is added to the blood circulation 512 through a substituate line (not shown).

In the dialyzer or hemofilter 513, a semipermeable membrane 511 separates a filtrate chamber 508 from a blood chamber 510. A fluid exchange or mass exchange from the from the blood chamber 510 into the filtrate chamber 508 takes place via the semipermeable membrane 511. The filtrate flow in the outlet line 505 from the filtrate chamber 508 is controlled by means of the variably adjustable throttle 517. The filtrate flowing out of the dialyzer or hemofilter 513 is detected by a flow meter 504 with regard to the filtrate flow rate and is generally discarded into a filtrate drain 502.

The pressure conditions on the membrane 511 in the hemofilter 513 are influenced through the control of the blood pump 515 or the control of the variably adjustable throttle 517 so that an excess pressure prevails in the blood chamber 510 in comparison with the filtrate chamber 508. There is therefore a transport of fluid through the membrane from the blood chamber 510 into the filtrate chamber 508.

For example, in one embodiment as a peristaltic pump, the blood pump can be controllable as operating parameters to achieve a certain pump rotational speed or a certain blood flow rate. Alternatively, the blood pump may also be controllable to achieve a certain delivery pressure as an operating parameter, for example, being controllable as an impeller pump.

The variably adjustable throttle 517 may be designed as a throttle with a variably adjustable cross section as a flow-through valve as a clocked valve or as some other component whose fluid resistance is adjustable in various positions, including a variably adjustable fluid resistance which is obtained only by averaging over time.

A control and regulating unit 501 connected to the flow meter 504 by a measurement line is connected to the blood pump 515 via the control line 513 and to the variably adjustable throttle 517 via the control line 516. During the blood treatment, current measurement parameters of hemofiltration such as the quantity of filtrate or the filtration rate are transmitted by the flow meter 504 to the control and regulating unit 501 either continuously or periodically. The control and regulating unit 501 uses the current measured parameters to derive control signals for the blood pump 515 and for the variably adjustable throttle 517. The blood pump 515 and the variably adjustable throttle 517 are controlled with regard to an ultrafiltration to be achieved, for example a certain filtration rate or a certain filtrate volume to be achieved over the course of treatment.

The regulation may take place in such a way that the blood pump 515 is operated at a constant rotational speed or at a constant delivery pressure, and the variably adjustable throttle 517 is controlled so that the measured value transmitted by the flow meter 504 serves as a manipulated variable. If the transmitted measured value of the filtration rate is above a corresponding setpoint value then the variably adjustable throttle 117 is to be constricted or in other words its flow resistance is to be increased. If the filtration rate is below its setpoint value, the variably adjustable throttle 517 is opened wider or in other words its flow resistance is reduced.

An alternative control strategy is such that the variably adjustable throttle 117 is set at a certain flow resistance and the blood pump 515 is controlled so that the filtration value transmitted by the flow meter 504 serves as a manipulated variable. If the transmitted value of the filtration rate is above a corresponding setpoint value, then the blood pump 507 is to be throttled. If the filtration rate is below its setpoint value, the blood pump 507 is accelerated.

The filtration may be regulated in such a way that a certain value is preselected for the filtration rate. Alternatively, a certain filtration profile may be preselected for the filtration volume to be withdrawn during the blood treatment.

Instead of the filtrate quantity, the quantity of substitute added through the substitute line during the treatment may be adjusted in a balance together with the quantity of filtrate withdrawn and the resulting ultrafiltration rate, i.e., the difference between the filtration rate and the substitute rate may be used as a control variable.

The preselected value of the ultrafiltration rate may be a constant value or a continuously variable value for the ultrafiltration rate.

The ultrafiltration may be regulated in this case by analogy with the control strategies described above for the ultrafiltration rate so that instead of a comparison with the setpoint value of the ultrafiltration rate, a corresponding comparison with an ultrafiltration profile is performed.

The invention claimed is:

1. A device (1, 2) for regulating an ultrafiltration in a dialysis treatment in which the blood to be ultrafiltered flows through a blood chamber (110) of a dialyzer (113) which is subdivided by a semipermeable membrane (111) into a blood chamber (110) and a dialysis fluid chamber (108) in an extracorporeal blood circulation (112), and dialysis fluid in a dialysis fluid circulation (109) flows through the dialysis fluid chamber (108) of the dialyzer (113), having a blood pump (115) for controlling a blood flow in the extracorporeal blood circulation (112), having a dialysis fluid pump (107) which is arranged in the dialysis fluid circulation (109) upstream from the dialyzer (113) for controlling a dialysis fluid flow in an inflow to the dialysis fluid chamber, having a variably adjustable throttle (117) arranged in the dialysis fluid circulation downstream from the dialyzer configured to control the dialysis fluid flow in the outflow out of the dialysis fluid chamber (108) by increasing and decreasing the resistance to dialysis fluid flowing out of the dialysis fluid chamber and through the throttle, said variably adjustable throttle having (1) a clocked valve or (2) a variably adjustable cross-sectional flow-through whose fluid resistance is adjustable solely through constricting or widening of the throttle, and without the inclusion of any fluid pumping mechanism in the dialysis fluid circulation downstream from the dialyzer, having a balancing device (104) configured to measure the fluid balance in the dialysis fluid circulation between the inflow (106) and the outflow (105) out of the dialysis fluid chamber (108) as a measure of the ultrafiltration, and for transmitting the measured fluid balance as an ultrafiltration parameter to a control and regulating unit (101), a control and regulating unit (101) configured to receive the ultrafiltration parameter from said balancing device and to regulate the throttle (117) so that a predetermined ultrafiltration value is achieved, said control and regulating unit connected to said throttle to provide control signals to the throttle, said throttle responsive to the control signals to control the dialysis fluid flow in said outflow, said control and regulating unit configured to control the throttle so that the ultrafiltration parameter measured and transmitted by the balancing device matches the predetermined ultrafiltration value.

2. The device (1, 2) according to claim 1, wherein a predetermined value can be set for the blood flow.

3. The device (1, 2) according to claim 1, wherein a predetermined value can be set for the dialysis fluid flow and the regulating unit is adjusted to regulate the blood flow.

4. The device (1, 2) according to claim 1, wherein a profile for the ultrafiltration rate can be preselected by the regulating unit (101) in which intervals with a positive ultrafiltration rate alternate with intervals having a negative ultrafiltration rate.

5. The device (1, 2, 51) according to claim 1, wherein the control and regulating unit (101) is adapted to preselect an ultrafiltration rate, a hemofiltration rate and/or an ultrafiltration volume or hemofiltration volume that is to be withdrawn during the course of treatment.

6. The device (1, 2, 51) according to claim 1, wherein the blood pump is arranged in an inlet line to the blood chamber.

7. The device (1, 2, 51) according to claim 1, wherein the throttle (117) is designed as a clocked valve.

8. The device according to claim 1, wherein the regulating unit is further configured to regulate the blood pump (115).

9. The device according to claim 1, wherein the regulating unit is further configured to regulate the dialysis fluid pump (107).

10. A device (1, 2) for regulating an ultrafiltration in a dialysis treatment in the blood to be ultrafiltered in an extracorporeal blood circulation (112) in which blood flows through a blood chamber (110) of a dialyzer (113) which is subdivided by a semipermeable membrane (111) into the blood chamber (110) and a dialysis fluid chamber (108), and dialysis fluid flows in a dialysis fluid circulation (109) through the dialysis fluid chamber (108) of the dialyzer (113), having a blood pump (115) for controlling a blood flow in the extracorporeal blood circulation (112), having a dialysis fluid pump arranged downstream from the dialyzer (113) in the dialysis fluid circulation (109) for control of a dialysis fluid flow in an outflow out of the dialysis fluid chamber, having a variably adjustable throttle arranged upstream from the dialyzer in the dialysis fluid circulation, said throttle configured to control the dialysis fluid flow in an inflow to the dialysis fluid chamber by increasing and decreasing the resistance to dialysis fluid flowing into the dialysis fluid chamber, said variably adjustable throttle having (1) a clocked valve or (2) a variably adjustable cross-sectional flow-through whose fluid resistance is adjustable solely through constricting or widening of the throttle, and without the inclusion of any fluid pumping mechanism in the dialysis fluid circulation upstream from the dialyzer, having a balancing device (104) configured to measure a liquid balance in the dialysis fluid circulation between the inflow (106) and the outflow (105) of the dialysis fluid chamber (113) as a measure of the ultrafiltration, and for transmitting the measured ultrafiltration to a control and regulating unit (101), a control and regulating unit (101) configured to receive the measured ultrafiltration and to regulate the throttle so that a predetermined ultrafiltration is achieved, said control and regulating unit connected to said throttle to provide control signals to the throttle, said throttle responsive to the control signals to control the dialysis fluid flow in said inflow, said control and regulating unit configured to control the throttle so that the measured and transmitted ultrafiltration of the balancing device matches the predetermined ultrafiltration value.

11. The device according to claim 10, wherein the regulating unit is further configured to regulate the blood pump (115).

12. The device according to claim 10, wherein the regulating unit is further configured to regulate the dialysis fluid pump (107).

13. A device (1, 2) for regulating an ultrafiltration in a dialysis treatment in which the blood to be ultrafiltered flows through a blood chamber (110) of a dialyzer (113) which is subdivided by a semipermeable membrane (111) into a blood chamber (110) and a dialysis fluid chamber (108) in an extracorporeal blood circulation (112), and dialysis fluid in a dialysis fluid circulation (109) flows through the dialysis fluid chamber (108) of the dialyzer (113), Having a blood pump (115) for controlling a blood flow in the extracorporeal blood circulation (112), Having a dialysis fluid pump (107) which is arranged in the dialysis fluid circulation (109) upstream from the dialyzer (113) for controlling a dialysis fluid flow in an inflow to the dialysis fluid chamber, Having a variably adjustable throttle (117) arranged in the dialysis fluid circulation downstream from the dialyzer configured to control the dialysis fluid flow in the outflow out of the dialysis fluid chamber (108) by increasing or decreasing the resistance to dialysis fluid flowing out of the dialysis fluid chamber and through the throttle, said variably adjustable throttle having (1) a clocked valve or (2) a variably adjustable cross-sectional flow-through whose fluid resistance is adjustable solely through constricting or widening of the throttle, Having a balancing device (104) configured to measure the fluid balance in the dialysis fluid circulation between the inflow (106) and the outflow (105) out of the dialysis fluid chamber (108) as a measure of the ultrafiltration, and for transmitting the measured fluid balance as an ultrafiltration parameter to a control and regulating unit (101), Wherein the balancing device has a differential flow-measuring unit (104) for measuring the differential flow between a flow in the inflow to the dialysis fluid chamber (108) and the outflow out of the dialysis fluid chamber, a branch from the inflow or the outflow to the branch of the dialysis fluid from the inflow or the outflow into another flow path (212) as well as a device for adjusting the flow rate (211) in the inflow, in the outflow and/or in the additional flow path, this measuring unit beign controllable so that the measured differential flow fulfills a predetermined condition, and having a device (211) for determining the flow rate in the additional flow path as a measure of the fluid balance, A control and regulating unit (101) configured to receive the ultrafiltration parameter from said balancing device and to regulate the throttle (117) so that a predetermined ultrafiltration value is achieved, Said control and regulating unit connected to said throttle to provide control signals to the throttle, said throttle responsive to the control signals to control the dialysis fluid flow in said outflow, Said control and regulating unit configured to control the throttle so that the ultrafiltration parameter measured and transmitted by the balancing device matches the predetermined ultrafiltration value.

14. The device (2) according to claim 13, wherein the predetermined condition of the differential flow is based on an integration of the differential flow over a predetermined integration interval.

15. A method for regulating an ultrafiltration in a dialysis treatment in which blood to be ultrafiltered in an extracorporeal blood circulation (112) flows through a blood chamber (110) of a dialyzer (113) which is subdivided by a semipermeable membrane (111) into a blood chamber (110) and a dialysis fluid chamber (108), and dialysis fluid in a dialysis fluid circulation (109) flows through the dialysis fluid chamber (108) of the dialyzer (113), and in which upstream from the dialyzer (113) there is a dialysis fluid pump (107) controlling a dialysis fluid flow in an inflow to the dialysis fluid chamber (108), downstream from the dialyzer there is a variably adjustable throttle (117) controlling the dialysis fluid flow in an outflow out of the dialysis fluid chamber (108), and without any additional dialysis fluid pump in the outflow of the dialysis fluid chamber, said variably adjustable throttle having (1) a clocked valve or (2) a variably adjustable cross-sectional flow-through whose fluid resistance is adjustable solely through constricting or widening of the throttle, a balancing device (104) measuring a fluid balance in the dialysis fluid circulation between the inflow and the outflow out of the dialysis fluid chamber (108) as a measure of the ultrafiltration and transmitting the measured fluid balance to a control and regulating unit (101), and a blood pump (107) controlling blood flow rate in the extracorporeal blood circulation (109) and wherein the method comprises regulating the throttle (117) by (1) regulating the clocking of the clocked valve or (2) constricting or widening the cross-sectional flow-through the throttle, and without any fluid pumping, said regulating by the control and regulating unit so that the ultrafiltration measured and transmitted by the balancing device achieves a predetermined ultrafiltration.

16. The method for regulating an ultrafiltration according to claim 15, wherein a profile for the ultrafiltration rate is preselected, in which intervals with a positive ultrafiltration rate alternate with intervals having a negative ultrafiltration rate.

17. The method for regulating an ultrafiltration according to claim 15, further comprising regulating the dialysis fluid pump (107).

18. The method for regulating an ultrafiltration according to claim 15, further comprising regulating the blood pump (115).

19. The method for regulating an ultrafiltration in a dialysis treatment in which blood to be ultrafiltered in an extracorporeal blood circulation (112) flows through a blood chamber (110) of a dialyzer (113) which is subdivided by a semipermeable membrane (111) into a blood chamber (110)

and a dialysis fluid chamber (108), and dialysis fluid in a dialysis fluid circulation (109) flows through the dialysis fluid chamber (108) of the dialyzer and in which a dialysis fluid pump is provided downstream from the dialyzer (113) to control the dialysis fluid flow in an outflow out of the dialysis fluid chamber, a variably adjustable throttle (117) is provided upstream from the dialyzer controlling the dialysis fluid flow in an inflow to the dialysis fluid chamber, and without any additional dialysis fluid pump in the inflow into the dialysis fluid chamber, said variably adjustable throttle having (1) a clocked valve or (2) a variably adjustable cross-sectional flow-through whose fluid resistance is adjustable solely through constricting or widening of the throttle, a balancing device (104) is provided for measuring a liquid balance in the dialysis fluid circulation (109) between the inflow and the outflow out of the dialysis fluid chamber (108) as a measure of the ultrafiltration, and transmitting the measured fluid balance to a control and regulating unit (101), and a blood pump (115) controlling a blood flow in the extracorporeal blood circulation and such that the method comprises regulating the throttle by (1) regulating the clocking of the clocked valve or (2) constricting or widening the cross-sectional flow-through the throttle, and without any fluid pumping, said regulating by the control and regulating unit so that the ultrafiltration measured and transmitted by the balancing device achieves a predetermined ultrafiltration.

20. The method for regulating an ultrafiltration according to claim 19, further comprising regulating the dialysis fluid pump (107).

21. The method for regulating an ultrafiltration according to claim 19, further comprising regulating the blood pump (107).

22. A method for regulating an ultrafiltration in a dialysis treatment in which blood to be ultrafiltered in an extracorporeal blood circulation (112) flows through a blood chamber (110) of a dialyzer (113) which is subdivided by a semipermeable membrane (111) into a blood chamber (110) and a dialysis fluid chamber (108), and dialysis fluid in a dialysis fluid circulation (109) flows through the dialysis fluid chamber (108) of the dialyzer (113), and a blood pump (107) controlling blood flow rate in the extracorporeal blood circulation (109), and in which upstream from the dialyzer (113) there is a dialysis fluid pump (107) controlling a dialysis fluid flow in an inflow to the dialysis fluid chamber (108), downstream from the dialyzer there is a variably adjustable throttle (117) controlling the dialysis fluid flow in an outflow out of the dialysis fluid chamber (108), said variably adjustable throttle having (1) a clocked valve or (2) a variably adjustable cross-sectional flow-through whose fluid resistance is adjustable solely through constricting or widening the throttle, a balancing device (104) measuring a fluid balance in the dialysis fluid circulation between the inflow and the outflow out of the dialysis fluid chamber (108) as a measure of the ultrafiltration and transmitting the measured fluid balance to a control and regulating unit (101), Wherein the balancing device has a differential flow measuring unit (104) for measuring the differential flow between a flow in the inflow to the dialysis fluid chamber (108) and the outflow out of the dialysis fluid chamber, a branch from the inflow or the outflow to the branch of the dialysis fluid from the inflow or the outflow into another flow path (212) as well as a device for adjusting the flow rate (211) in the inflow, in the outflow and/or in the additional flow path, this measuring unit being controllable so that the measured differential flow fulfills a predetermined condition, and having a device (211) for determining the flow rate in the additional flow path as a measure of the fluid balance and wherein the balancing between an inflow and an outflow from the dialysis fluid chamber, the method comprising, Measuring a differential flow between an inflow to the dialysis fluid chamber (108) and an outflow out of the dialysis fluid chamber, Using the measured differential flow as a control variable for the device for setting a flow rate in another flow path (212) which branches off from the inflow or the outflow and determining the flow rate in the additional flow path as a measure of the fluid balance, and wherein the method further comprises regulating the throttle (117) by (1) regulating the clocking of the clocked valve or (2) constricting or widening the cross-sectional flow-through the throttle, said regulating by the control and regulating unit so that the ultrafiltration measured and transmitted by the balancing device achieves a predetermined ultrafiltration.

23. The method for regulating an ultrafiltration according to claim 22, wherein a predetermined condition is fulfilled for the differential flow, based on integration of the differential flow over a predetermined integration interval.

* * * * *